United States Patent [19]

Johnson et al.

[11] Patent Number: 5,130,118

[45] Date of Patent: Jul. 14, 1992

[54] METHODS AND MATERIALS FOR THE PREPARATION OF METAL LABELLED ANTIBODY SOLUTIONS

[75] Inventors: David K. Johnson, Vernon Hills; Patrick E. Rogers, Grayslake, both of Ill.

[73] Assignee: Abbott Laboratories, Abbott Park, Ill.

[21] Appl. No.: 118,148

[22] Filed: Nov. 6, 1987

[51] Int. Cl.$^5$ ............................................. A61K 43/00
[52] U.S. Cl. ............................................. 424/1.1; 424/9;
424/6; 424/85.8; 424/85.91; 436/64; 436/173; 436/175; 436/547
[58] Field of Search ...................... 424/9; 436/519, 63, 436/64, 173, 175; 514/6; 530/389

[56] References Cited

U.S. PATENT DOCUMENTS

| | | | |
|---|---|---|---|
| 4,454,106 | 6/1984 | Gansow et al. | 424/9 |
| 4,472,509 | 9/1984 | Gansow et al. | 424/9 |
| 4,634,586 | 1/1987 | Goodwin et al. | 435/35 X |

OTHER PUBLICATIONS

Esteban et al., "New Method for Chelation of Indium-111 ...", J. Nucl. Med. 28(5), 861–870 (1987, May).

*Primary Examiner*—Sam Rosen
*Attorney, Agent, or Firm*—Wean Khing Wong; Lawrence S. Pope; Daniel R. Curry

[57] ABSTRACT

The present invention provides a metal ion scavenging procedure and antibody compositions for radioimmunoscintigraphy and cytotoxic radioimmunotherapy having chelator concentrations of greater than about $10^{-4}$ M which are optimized with respect to their metal binding capacity such that highly efficient labelling of the antibody is achieved in a simple one step procedure using readily available sources of radiometal ions.

36 Claims, No Drawings

METHODS AND MATERIALS FOR THE PREPARATION OF METAL LABELLED ANTIBODY SOLUTIONS

BACKGROUND

The present invention relates generally to metal-binding conjugates of antibodies and antibody fragments which are useful in a variety of diagnostic and therapeutic techniques. Specifically, the invention relates to methods for the preparation of improved aqueous solutions of chelator/antibody conjugates and metal ion/chelator/antibody conjugates.

In recent years significant progress has been made in efforts to produce pharmaceutical agents comprising conjugates of radioisotopic and other metal ions with monoclonal antibodies. The ability of monoclonal antibodies to bind with high specificity to selected antigenic epitopes provides a means by which specified metal ions may be selectively directed to target tissues. Conjugates of radioisotopic metal ions with monoclonal antibodies capable of selective binding with tumor and other disease associated antigens are contemplated to be of particular utility for use in diagnostic imaging and radiotherapy protocols for the diagnosis and treatment of conditions such as cancer.

Where antibody-metal ion conjugates are to be used for the therapeutic delivery of cytotoxic radiation the metal is generally selected from a beta-particle emitter such as yttrium. Order, et al., Int. J. Radiation Oncology Biol. Phys., 12, 277-81 (1986) describes treatment of hepatocellular cancer with antiferritin polyclonal antibodies to which $^{90}$yttrium has been chelated. Buchsbaum, et al., Int. J. Nucl. Med. Biol., Vol. 12, No. 2, pp. 79-82, 1985 discloses radiolabelling of monoclonal antibodies to CEA with $^{88}$yttrium and suggests the possibility of localization and treatment of colorectal cancers therewith. Nicolotti, EPO Application No. 174,853 published Mar. 19, 1986, discloses conjugates comprising metal ions and antibody fragments. According to that disclosure, monoclonal antibodies of subclass IgG are enzymatically treated to remove the Fc fragment and reductively cleave the disulfide bond linking the antibody heavy chains. The Fab' fragment is then linked to a chelating agent bound to a radionuclide metal ion for in vivo diagnostic or therapeutic use.

Where antibody conjugates are to be used for diagnostic radioimaging (radioimmunoscintigraphy) purposes a gamma emitting radioisotope is preferably selected. Goldenberg, et al., N. Eng. J. Med., 298, 1384-88 (1978) discloses diagnostic imaging experiments wherein antibodies to the known tumor associated antigen carcinoembryonic antigen (CEA) are labelled with $^{131}$iodine and injected into patients with cancer. After 48 hours, the patients are scanned with a gamma scintillation camera and tumors are localized by the gamma emission pattern. Gansow, et al., U.S. Pat. No. 4,454,106 discloses the use of monoclonal antibody/metal ion conjugates for in vivo radioimaging diagnostic methods.

U.S. Pat. No. 4,472,509, Gansow, et al., discloses the use of diethylenetriaminepentaacetic acid (DTPA) chelating agents for the binding of radiometals to monoclonal antibodies. The patent is particularly directed to a purification technique for the removal of non-bonded and adventitiously bonded (non-chelated) metal from radiopharmaceuticals but is illustrative of art recognized protocols for preparation of radioisotopic pharmaceuticals. According to such general procedures, an antibody specifically reactive with the target tissue associated antigen is reacted with a quantity of a selected bifunctional chelating agent having protein binding and metal binding functionalities to produce a chelator/antibody conjugate. In conjugating the antibodies with the chelators an excess of chelating agent is reacted with the antibodies, the specific ratio being dependent upon the nature of the reagents and the desired number of chelating agents per antibody. Gansow, et al., disclose chelator to antibody ratios of 100:1 to 600:1 as being particularly useful according to one system for achieving from about 0.5 to 1.5 bound chelators per molecule. The reference cautions, however, that care must be taken not to add so many chelators per antibody molecule so as to adversely affect the immunoreactivity of the antibody. After conjugation of the chelators with the antibodies, the reaction mixture is purified to remove excess decomposed chelator. The Gansow reference discloses purification by dialysis of the conjugate mixture over a 48 hour period against three changes of solution comprising 50 mM citrate and 200 mM sodium chloride with 1 ml of gel resin. The reference also discloses an optional first dialysis step which may be carried out against a dilute solution of ascorbic acid (30 mM) and ethylenediaminetetraacetic acid (EDTA) chelating agent (5 mM) "to remove any residual iron which may be present in the chelate or the protein."

The purified chelator/antibody conjugate may then be conjugated with the active metal label or stored until later use. A solution of metal label is obtained from a source such as a radioisotope generator or accelerator according to known methods. Metal chelation is then carried out in an aqueous solution with pHs generally ranging from about 3.2 to about 9 so as not to impair the biological activity or specificity of the antibodies. Weakly chelating acids and bases such as citric acid and glycine are employed as buffers. The metal ions are generally introduced in the form of metal salts such as metal halides, nitrates or perchlorates with chlorides being particularly preferred. The reference suggests that the metal salt be employed in as high a concentration as is practicable although it notes that when radioactive metals are used, health and safety considerations recommend use of a metal concentration below one equivalent of metal per chelate binding site.

Gansow, et al., state that metal ion/chelator/antibody conjugates so prepared will generally require purification prior to their administration in vivo in order to remove free and adventitiously bonded metal. The patent discloses various techniques involving a combination of ion exchange and gel filtration chromatography. A preferred procedure involves passing an aqueous solution containing the conjugate through a chromatography column with two layers, a first layer selected from a group consisting of an anion exchange resin, a cation exchange resin and a chelating ion exchange resin and a second layer comprising a sizing matrix. Such a procedure is said to result in solutions which showed less than a six percent (6%) loss of indium when dialyzed against a buffer comprising 20 mM 2-(N-morpholino)ethane sulfonic acid) (MES) and 200 mM sodium chloride at pH 6.0.

Numerous variations on the general methods disclosed above are known for the covalent labelling of antibodies and antibody fragments with metal chelating moieties. Such methods include those whereby the labelling proceeds via a mixed anhydride as disclosed by Krejcarek, et al., Biochem. Biophys. Res. Commun., 77, 581 (1977), via a bicyclic anhydride as described by Hnatowich, et al., J. Immunol. Methods, 65, 147 (1983) or via an active ester as described by Paxton, et al., Cancer Res., 45, 5694 (1985).

The methods of Gansow, et al., as are those of other workers in the field, are controlled by several purity related concerns relating to the preparation of metal ion/chelating agent/antibody conjugates for in vivo administration. It is axiomatic that the quantity of active metal (as distinguished from other metal impurities present in the conjugate solution in either free, adventitiously bound or chelated form) delivered to target tissues be maximized. It is similarly the case that the quantity of active metal delivered to non-target tissues be minimized. In diagnostic imaging protocols this is the case as a consequence of the desire to minimize background signals. In cytotoxic radiotherapy protocols, this is a consequence of concerns relating to cytotoxic effects on non-target tissues. An additional concern relates to the desire that the quantity of antibody conjugates be minimized in these protocols in order to minimize the antigenic effects of in vivo introduction of protein.

The goal of directing a maximum quantity of active metal to the target tissue is affected by a number of factors. Foremost of these factors are the specificity and activity of the antibody. The antibody or antibody fragment upon which the conjugate is based must have high binding activity and selectivity for the target antigen. In addition, the antigen to which the antibody is specifically targeted must be selected such that the antigen has a high specificity for the tissue to be targeted as opposed to other tissues.

Given an antigen that is highly specific for the target tissue and an antibody with high activity and selectivity for that antigen, it is then a significant concern that the immunoreactivity of the antibody making up the conjugate not be diminished by virtue of some chemical alteration occurring during the process of forming the chelator/antibody conjugate or in the metal chelating step. Chemical alteration resulting in partial or total loss of immunological activity may occur as a consequence of high temperature, extremely acidic or alkaline pH or other chemical treatment. Such alteration may, in the extreme, result in denaturation of the antibody molecule. Alteration less extreme than denaturation may occur where the protein binding groups of bifunctional chelating agents react and link with amino acid residues or with glycosylation on the antibody molecules in such a manner that the specific binding regions of the antibody are altered or sterically blocked. The higher the chelator to antibody substitution level in any given chelator/antibody system, the greater the likelihood that such loss of immunoreactivity will occur.

A corollary to the desire to maximize the delivery of the active metal to the target tissue is the desire to minimize the delivery of the active metal to nontarget tissue. It is the case that active metal which goes to target tissues is almost invariably bound by means of a chelating agent to an antibody specific for that tissue. By contrast, the bulk of active metal which is delivered to nontarget tissues is free metal, metal which was covalently bound to an antibody which was not delivered to the target tissue or adventitiously bound metal which became free of the antibody in vivo. Active metal which is adventitiously bound or free in solution will frequently, upon administration to the patient, become rapidly bound to serum transferrin and be subsequently distributed primarily to the liver and bone marrow leading to undesirable nontarget accumulation of the radiometal. The presence of free metal in radioisotopic preparations for administration in vivo is of particular concern where the toxic effects of concentrating such metals at the liver and other nontarget organs stands to present major limitations to the use of such radioisotopic pharmaceuticals.

With respect to any preparation for administration in vivo it is particularly desired to minimize the quantity of antibodies utilized to deliver a quantity of active metal. This results from concerns related to the antigenicity of the antibodies and antibody fragments used to deliver active metals and the possibility of immune reactions to the pharmaceutical preparation itself. Efforts to minimize the quantity of antibodies introduced by increasing the quantity of metal ions bound to each antibody tend to be limited by the tendency of antibodies to denature or lose specific binding activity at elevated levels of chelating agent substitution.

A significant factor bearing on the various concerns recited above relates to the extremely high concentrations of impurities found in radiometal preparations available for conjugation with chelator/antibody conjugates. Of interest to the present invention is the disclosure of Hnatowich, et al., J. Immunol. Methods, 65, 147 (1983) which states that an antibody/chelator composition with a 1:1 chelator to antibody ratio and labelled with indium-111 (35 mC;/mg) has only 4% of the available chelating sites occupied by indium-111 atoms. The metal impurities present at elevated levels in available radiometal preparations effectively compete against the active label metals for binding sites on the chelator/antibody conjugates. The presence of such impurities mandates the use of chelator/antibody conjugates in quantities far greater than would be required to simply chelate a given amount of the pure metal label. The requirement of adding increased quantities of metal solution to assure chelation of a specified amount of active metal is undesirable because to do so results in the presence of greater quantities of free and adventitiously bonded metal which must generally be chelated or removed from the conjugate solution prior to administration in vivo. Use of greatly increased quantities of the chelator/antibody conjugates to chelate sufficient label is also undesirable because of the increased antigenicity of the administered dose.

Efforts to purify radiometal solutions prior to chelation with the conjugate solution have been disclosed as have been efforts to reduce the extent of prelabelling chelation of free chelator groups in the chelator/antibody conjugate. Meares, et al., Anal. Biochem., 142, 68 (1984) discloses the preparation of bifunctional EDTA analogues bearing isothiocyanate and bromoacetamide derivatives as substrate reactive groups. The chelator/antibody conjugates were labelled with indium-111 and other metal ions. The reference discloses the use of elaborate precautions to minimize metal contamination when performing the conjugate forming and coupling procedures. Such precautions include the use of high purity water, metal-free buffer salts and acid-washed glassware and are useful for limiting the concentration of metal contaminants which compete for chelating sites with the desired metal. The reference also discloses the purification of commercially available $^{111}InCl_3$ solutions by anion-exchange chromatography to remove many of the contaminating metals present in the commercially available solution.

According to one procedure, Meares, et al., discloses preparation of the bromoacetamide analog of EDTA and its reaction with a mouse monoclonal antitransferrin receptor antibody solution at a 10:1 molar ratio. After incubation at 37° C. for two hours, the reaction mixture was removed and applied to a Sephadex G-50-80 centrifuge column prepared with 0.1 M ammonium citrate (pH 6) and a gel filtration step was carried out to remove unbound chelator. The purified chelator/antibody product had a concentration of $9.5 \times 10^{-5}$ M which with a chelator/antibody ratio of 1.3:1 provided a chelator concentration of $1.24 \times 10^{-4}$ M.

Carrier-free $^{111}$indium stock solutions were prepared by adding to an ammonium citrate buffer solution an $^{111}$InCl$_3$ solution which had been purified by treatment in a Bio-Rad AG1-X4 anion exchange column equilibrated with 2 M HCl. Two 10 μl aliquots of the $^{111}$indium solution were mixed with 5 μl aliquots of the EDTA/antibody solution and allowed to incubate for periods of time ranging from 5 to 80 minutes. An EDTA challenge procedure was carried out against samples of the indium/chelator/antibody conjugates in order to scavenge any free or adventitiously bound metal from the conjugate solution. One μl aliquots of the conjugate solutions were contacted with 5 μl aliquots of a 10 mM solution of Na$_2$ EDTA challenge solution. The solutions so treated were then subjected to a thin layer chromatography (TLC) procedure by which antibody-bound metal was separated from free and chelator bound metal in order to determine the quantity of nonspecifically bound indium. The reference reported that the amount of unbound indium being transported on the TLC plate was only 3 to 5% of the total indium thus indicating that the radiochemical yield of the metal chelation procedure was 95 to 97%.

Meares, et al., state that in procedures where the metal ion is to be added last after preparation of the antibody/chelator conjugate that it is preferred that the concentration of protein bound chelating groups be greater than $10^{-5}$ M in order that the added metal ions may be bound quickly and quantitatively. The reference states that with antibody concentrations in excess of 15 mg/ml ($10^{-4}$ M) that the preferred conditions may be achieved.

Goodwin, et al., J. Nuc. Med., 26, 493-502 (1985) discloses further work of the Meares group wherein bromoacetamidobenzyl-EDTA was conjugated to mouse monoclonal antibodies specific for the mouse major histocompatibility complex alloantigen IA$^k$ according to the method of Meares, et al. described earlier. The antibodies are present at a concentration of $1.5 \times 10^{-4}$ M which with a chelator to antibody ratio of 3.3:1 resulted in a $5 \times 10^{-4}$ M concentration of chelators.

Radiolabelling was performed by combining small (10 to 50 μl) aliquots of the antibody/chelator conjugate with 50 μl aliquots of purified $^{111}$indium citrate at pH 5.0. Chelation of the indium to the chelator/antibody conjugate was said to go to completion in less than 5 minutes. The reference indicated that the indium label could not then be removed from the conjugate even with a greater than thousand-fold challenge with EDTA. Labelling efficiency and radio-chemical yield were measured by the EDTA challenge/thin layer chromatography procedure of Meares, et al. which indicated radiochemical yields ranging from 85 to 95%.

In some experiments unbound metal was complexed with an EDTA chase. In other experiments, the indium/chelator/antibody solution containing unbound metal was diluted in phosphate buffered normal saline containing 0.1% human serum albumin, 0.1 M sodium citrate and 0.01 M EDTA which bound free metal but was not removed prior to intravenous injection. It is understood that the theory behind the addition of unconjugated chelators to the solution is that such agents will chelate with free and adventitiously bound metals and that the resulting chelate when administered in vivo will be rapidly cleared from the circulation by way of the kidney. The reference discloses animal biodistribution studies with the indium/chelator/antibody conjugate. Organ distribution studies after 24 hours showed spleen uptakes in excess of about 100% dose per gram of organ for antigen positive mice although spleen uptakes were lower for antigen negative mice and in systems where the conjugate comprises a normal mouse IgG. The reference noted that indium chelates have increased stability over radioiodine preparations and that such stability produces not only increased target concentrations but also higher nonspecific blood and liver activity.

Of interest to the present invention is the disclosure of Zoghbi, et al., Invest. Radiol., 21, 710 (1986) which relates to procedures for the purification of indium-111. The reference notes that there is large variability in the purity of commercially available indium and that variability in the quantities of indium chelated by chelators such as DTPA (well below the capacity of the ligands) may be explained by the presence of cationic contaminants such as zinc, iron and aluminum in commercial indium preparations and the fact that the chelators are not specific for indium. The reference reports that $^{111}$indium purified according to a solvent extraction procedure disclosed by the reference exhibits more than a threefold increase in the specific activity of an $^{111}$In-DTPA-monoclonal antibody over $^{111}$indium which was not purified.

Later references by the Gansow group disclose various post-chelation step purification procedures for the indium/chelator/conjugate solutions. Brechbiel, et al., Inorg. Chem., 25, 2772 (1986) and Esteban, et al., J. Nucl. Med., 28, 861 (1987), compare several different procedures for removing unbound indium-111 from the monoclonal antibody B72.3. Brechbiel, et al., compares (1) the EDTA chase method of Goodwin, et al., (2) gel column chromatography, (3) high performance liquid chromatography (HPLC) and (4) the combination of gel column chromatography and HPLC purification. The reference states that the simple addition of free EDTA to the mixture was not sufficient to remove all unreacted $^{111}$indium by localization and passage through the kidneys but that instead the metal tended to localize in the liver. The preferred method for purification of the conjugate solutions was stated to be passage through a Sephadex G-50 column followed by HPLC purification on a TSK-3000 sizing column. Treatment by HPLC was stated to be the only method for removal of "high-molecular weight" aggregates such as crosslinked chelating moieties. The reference recommends use of the strongest possible chelating agent in combination with mild coupling techniques and the best purification techniques.

Esteban, et al., J. Nucl. Med., 28, 861 (1987) provided description of additional purification and biodistribution studies of the Gansow group with the B72.3 monoclonal antibody. Chelator/antibody conjugates with bifunctional DTPA and EDTA were formed at various substitution ratios. The antibody-chelate immunoreactivity was found to vary significantly with the molar ratio with the conjugates retaining 100% of their immunoreactivity when compared to unmodified IgG at 1:1 ratios. Chelator to antibody ratios of 3:1 or greater resulted in the loss of over 50% of immunoreactivity. Biodistribution studies were conducted with indium labelled conjugates having chelator to antibody ratios of 1:1. The reference confirmed the statement of the Brechbiel, et al., reference that the use of excess EDTA to chelate free metal in the conjugate solution provided poor purification with tumor to liver ratios of less than 1.6:1 while the use of labelled conjugates purified by HPLC resulted in tumor to liver ratios of 4.6:1.

Of interest to the present invention are references relating to efforts to systematically establish the maximum number of chelating groups which may be incorporated into each antibody molecule. Paik, et al., J. Nucl. Med., 24, 1158 (1983) and J. Nucl. Med., 24, 932 (1983) disclose the optimization of, respectively, bicyclic DTPA anhydride coupling to monoclonal antibody 17-1A and mixed anhydride coupling of DTPA to a monoclonal antibody to human serum albumin. Generally, however, those skilled in the art have felt little need to push substitution levels beyond one chelating group per antibody molecule since indium-111 is readily available in carrier-free form.

These various procedures involving prelabelling purification of the metal ion solution or post-labelling chasing or purification of the metal ion/chelator/antibody conjugate solution are time consuming and difficult to perform under conditions which preserve the sterility and apyrogenicity essential to an injectable radiopharmaceutical for human use. Moreover, the setting in which such antibody radiolabelling procedures are to be routinely performed is typically that of a hospital nuclear pharmacy and such facilities frequently lack the equipment and trained personnel to carry out the most preferred yet most complex post-purification techniques such as HPLC and gel chromatography.

SUMMARY OF THE INVENTION

The invention provides improved methods, compositions and kits for the preparation of metal ion/chelator/antibody conjugate solutions for radioimmunoscintigraphy. The methods and compositions of the invention are not limited to use in conjunction with radioimmunoscintigraphy, but are contemplated to be of use for a variety of applications including those such as in vivo cytotoxic radiotherapy. Specifically, the invention provides methods for the removal of free, adventitiously bonded and chelated metal ions from a solution of chelator/antibody conjugate comprising the steps of: (a) exposing the solution of chelator/antibody conjugate to a solution of unconjugated chelating agent with a concentration greater than about 0.01 M in a weakly chelating buffer for a period greater than about 12 hours, and (b) separating the chelator/antibody conjugate from the solution of unconjugated chelating agent. It is to be understood that the solution of unconjugated chelating agent will generally comprise the agent in the form of both chelators (metal-free) and chelates (metal-bound). The unconjugated chelating agent exposed to the chelator/antibody conjugate solution in step (a) is preferably as free of metals as is possible. By contrast, the solution of unconjugated chelating agent from which the conjugate solution is separated in part (b) will include proportions of the chelating agent in its metal-bound chelate form as a consequence of scavenging metal impurities from the conjugate solution.

The invention further provides solutions of a chelator/antibody conjugate characterized by having a chelator concentration of greater than about $10^{-4}$ M and produced according to the process of: (a) exposing a solution of chelator/antibody conjugate to a solution of unconjugated chelating agent with a concentration greater than about 0.01 M in a weakly chelating buffer for a period greater than about 12 hours, (b) separating the chelator/antibody conjugate from the solution of unconjugated chelating agent, and (c) adjusting the concentration of the antibody bound chelating groups to greater than about $10^{-4}$ M.

The invention also provides a method of preparing an aqueous solution of $^{111}$indium/chelator/ antibody conjugate comprising less than about 5% free or adventitiously bonded metal ions and suitable for in vivo administration for radioimmunoscintigraphy. The method is particularly useful for preparation of indium radioimmunoscintigraphy agents for use whereby post-chelation purification steps are not required to render the agent suitable for administration in vivo. According to the method, a first solution of a chelator/antibody conjugate characterized by having a chelator concentration of greater than about $10^{-4}$ M and being treated according to the above described procedure is contacted under conditions selected for chelation of indium ions with a second solution of commercially available $^{111}$indium salt characterized by a radioactivity of greater than about 30 mCi/ml wherein the ratio by volume of the first solution to the second solution is greater than about 5 to 1 and wherein the solutions are incubated for a period of less than about 30 minutes. The volume ratio of first solution to second solution is preferably from about 5 to 1 to about 20 to 1 and most preferably from about 7 to 1 to about 15 to 1. $^{111}$Indium/chelator/antibody conjugate solutions produced according to the above methods are characterized by the ability, without further purification, to deliver 48 hours after intravenous injection to a nude mouse no more than 10% of said indium per gram of tissue to the liver, spleen and kidney of said mouse.

The invention further provides "hot" and "cold" kits for preparation of injectable solutions of indium labelled antibody. Cold kits according to the invention include (1) a sterile apyrogenic solution of chelator/antibody conjugate characterized by having a chelator concentration of greater than about $10^{-4}$ M and produced according to the process of: (a) exposing a solution of chelator/antibody conjugate to a solution of unconjugated chelating agent with a concentration greater than about 0.01 M in a weakly chelating buffer for a period greater than about 12 hours, (b) separating the chelator/antibody conjugate from the solution of unconjugated chelating agent, and (c) adjusting the concentration of the antibody bound chelating groups to greater than about $10^{-4}$ M; and (2) a container which preserves the sterility and apyrogenicity of the solution and has provision for the aseptic introduction of the metal and aseptic removal of the labelled antibody. Hot kits according to the invention include (1) a sterile apyrogenic aqueous solution of a metal ion/chelator/antibody conjugate produced by chelation of a first metal ion solution with a second solution of a chelator/antibody conjugate characterized by having a chelator concentration of greater than about $10^{-4}$ M and produced according to the process of: (a) exposing a solution of chelator/antibody conjugate to a solution of unconjugated chelating agent with a concentration greater than about 0.01 M in a weakly chelating buffer for a period greater than about 12 hours, (b) separating the chelator/antibody conjugate from the solution of unconjugated chelating agent, and (c) adjusting the concentration of the antibody bound chelator groups to greater than about $10^{-4}$ M; and (2) a container which preserves the sterility and apyrogenicity of the solution and has provision for removal of the labelled antibody.

DETAILED DESCRIPTION

The present invention provides methods, compositions and kits for the production of metal labelled radiopharmaceuticals for use in radioimmunoscintigraphy and radioimmunotherapeutics. The invention provides a metal scavenging procedure for the removal of free, adventitiously bonded and chelated metal ions from a solution of a chelator/antibody conjugate. This method provides for chelator/antibody conjugates with improved metal label binding capacity as a consequence of having reduced levels of free and adventitiously bonded metal and elevated levels of free chelator. Chelator/antibody conjugate solutions with chelator concentrations in excess of about $10^{-4}$ M exhibit unexpected improved properties when subjected to the method of the invention. The resulting chelator/antibody solutions are characterized by a high metal binding capacity and are capable of rapidly chelating free metal ions to achieve high radiochemical yields when incubated under chelating conditions with solutions of radiometal which typically contain significant levels of metal impurities As one aspect of the invention, it has been discovered that chelator/antibody conjugate solutions with chelator concentrations greater than about $10^{-4}$ M which have been subjected to the scavenging method of the invention are capable, when incubated for 30 minutes or less under chelating conditions with commercially available indium chloride compositions, of yielding solutions of indium/chelator/antibody conjugates with radiochemical yields in excess of 95%. Such compositions generally do not require further purification in order to be suitable for human in vivo administration. The selection of chelator/antibody conjugates having a chelator concentration in excess of $10^{-4}$ M is based on the following findings. Firstly, there exists for any given chelator/antibody conjugate labelled under a fixed set of conditions, a critical chelator concentration below which, under these conditions, it is impossible to achieve effective radiolabelling and above which acceptable radiolabelling yields are achieved. This threshold concentration range is unexpected narrow, a 2-fold difference in the concentration of antibody-bound chelating groups often corresponding to the difference between a fully acceptable radiochemical yield (>90%) and a completely unacceptable yield (20-30%). Secondly, and even more unexpectedly, this critical threshold concentration of bound chelators varies from one antibody conjugate to the next, even though the same chelator is used to prepare both chelator/antibody conjugates. Thus, to assure satisfactory radiochemical yields from a general procedure applicable to any given antibody system, a concentration of antibody-bound chelators must be chosen which lies well outside the range of critical chelator concentrations observed for various antibodies. Based on studies conducted, it appears that about $10^{-4}$ M constitutes such a molar concentration of chelator.

The capability of reacting chelator/antibody solutions with indium metal salt solutions in a one step procedure to produce an indium/chelator/antibody conjugate solution suitable for human in vivo administration is a significant advance over the art in that it avoids complex, expensive and time consuming post-labelling purification steps or the addition of a scavenging chelator heretofore required to render the materials suitable for human administration. The chelator/antibody conjugate solutions of the present invention, further have the capability, when reacted with solutions of indium metal chloride of producing indium/chelator/antibody conjugates which when administered in vivo, deliver reduced levels of indium to the liver, spleen and kidneys of test animals injected therewith.

The present invention is based on the recognition of several limitations in present methods for the preparation of antibody/chelator/metal ion preparations. One limitation relates to antibody-chelator compositions prepared using the standard precautions to prevent contamination with adventitious metal ions and centers on the finding that, despite taking the best precautions possible, metal contamination is not completely eliminated during the conjugate preparation stage. One aspect of the present invention therefore relates to procedures for removing residual metal contaminants from antibody/chelator compositions subsequent to their preparation.

The invention is also based on the observation that even when the chelating groups in an antibody-chelator composition are rendered completely free from metal contaminants acquired during its preparation, the quantities of non-radioactive metals present in many commercial radiometal preparations such as indium-111 chloride are such as to effectively compete for the available chelating sites. Such competition is sufficiently severe at a substitution level of one chelator per antibody molecule that a poor radiochemical yield often results.

It is contemplated that the chelator/antibody conjugate solutions produced according to the invention will exhibit improved properties when incubated with metal ion preparations other than $^{111}$indium. While the specific chelator concentration and required incubation time may vary as a consequence of specific chelator to metal binding affinities and the identity and concentration of metal impurities present in differing metal ion preparations, it is contemplated that the chelator/antibody conjugate solutions of the present invention will exhibit improved radiochemical yields in binding procedures with other metals.

Chelator conjugate solutions having high concentrations of metal free chelators are useful not only because of their ability to achieve high radiobinding yields, but also as a consequence of their ability to minimize the amount of antibody or antibody fragment required to deliver a specific amount of active metal. Such is an important concern where repeated exposure to foreign protein is likely to provoke an adverse immunological response.

The chelator/antibody solutions of the invention having high free chelator concentrations are produced by maximizing the concentration of the chelator/antibody conjugates in solution and maximizing the substitution level of chelators per antibody to the greatest extent possible consistent with maintaining antibody activity and specificity. Even when concentration and chelator substitution levels are maximized it is additionally required that the chelator/antibody conjugate solution be subjected to the scavenging procedure which renders the solution and the chelator/antibody conjugate substantially free of metal. Maximization of the conjugate concentration is primarily dependent on antibody solubility with maximum concentrations generally approaching about $10^{-4}$ M. The precise concentration will, however, be dependent upon the specific nature of the antibody and the chelator system. Given maximization of the chelator/antibody concentration, it is also generally necessary to maximize the average number of chelating moieties per antibody. In maximizing the substitution level of antibodies, however, particular care must be taken to maintain antibody activity and specificity.

Those of skill in the art will recognize that antibodies differ greatly in their susceptibility to loss of immunoreactivity during chemical modification with chelating groups and hence that the maximum number of metal binding groups which may be introduced without loss of antibody immunoreactivity will vary from antibody to antibody. Nevertheless, within the constraints imposed by the foregoing, certain embodiments are preferred for all antibody compositions. Preferred compositions include those containing an average of from about 2 to about 15 chelating groups per antibody molecule, with compositions containing from about 3 to about 5 chelators per antibody being particularly preferred. Such compositions are preferably maintained at a high antibody concentration in a weakly chelating buffer in order to facilitate labelling. Preferred compositions contain the antibody or its fragment at a concentration between 5 mg/ml and 20 mg/ml in 0.01 to 0.5 M citrate buffer, pH 6.0.

Antibodies

Antibodies useful with the present invention include those of various types including IgA, IgD, IgE, IgG and IgM. The antibodies may be directed against a variety of antigenic determinants including those associated with tumors, histocompatibility and other cell surface antigens, bacteria, fungi, viruses, enzymes, toxins, drugs and other biologically active molecules. As an important aspect of the present invention relates to the detection and treatment of tumors, antibodies specifically reactive with tumor associated antigens are of particular interest to the present invention. Antigens associated with tumors for which antibodies may be specifically reactive include antigens as are described in Zalcberg and McKenzie, J. Clin. Oncology, Vol. 3; pp. 876-82 (1985) and include, but are not limited to, carcinoembryonic antigen (CEA), mucins such as TAG-72, human milk fat globule antigens and receptors such as the IL-2 and transferrin receptors. Antibodies which recognize such antigens may be monoclonal or polyclonal or made by recombinant techniques such as described in Morrison, et al., Proc. Nat. Acad. Sci. U.S.A., 81, 6851-55 (1984).

"Antibody" as used herein also refers to fragments of antibody molecules including half antibody molecules and Fab, Fab' or F(ab')$_2$ fragments. Nicolotti, EPO 174,853 published Mar. 19, 1986 hereby incorporated by reference, discloses methods by which entire antibodies are treated to effect a site specific cleavage of the two heavy chains, removing the F$_c$ portion of the carboxyl terminal ends of the heavy chains.

The antibodies should be capable of containing an average of about 2 to as many as 15 chelating groups per molecule, although antibodies capable of accommodating an average of about 2 to about 5 chelating groups per molecule are suitable to use with the invention. Preferred antibodies include those which are capable of accommodating an average of from about 3 to about 5 chelators per antibody without adversely affecting the immunoreactivity of the antibody.

Chelating Agents

A wide variety of chelating agents may be incorporated in the compositions of, and used according to, the methods of the present invention. While the specific choice of chelating agent is dependent upon a number of factors including the identity of the metal ion to be bound, a number of chelating agents are generally suitable for use with the invention. Such chelating agents should have high binding efficiencies and include bifunctional derivatives of diethylenetriaminepentaacetic acid (DTPA) and ethylenediaminetetraacetic acid (EDTA). Bifunctional derivatives of DTPA wherein para-aminophenyl substituents are attached to the methylene carbons of the polyamine backbone are described by Brechbiel, et al., Inorg. Chem., 25, 2772-81 (1986). Bifunctional derivatives of EDTA bearing a para-aminophenyl protein reactive substituent are described by Sundberg, et al., J. Med. Chem., 17, 1304 (1974). Particularly preferred bifunctional derivatives of DTPA and EDTA are described by co-owned and copending U.S. Application Ser. No. 014,517, filed Feb. 13, 1987 the disclosure of which is hereby incorporated by reference.

Other chelating agents contemplated to be of use according to the present invention include the cyclic chelating agent cyclohexane-1,2-transdiaminetetraacetic acid, Kroll, et al., Nature, 180, 919-20 (1957); macrocyclic chelating agents such as 6-(p-nitrobenzyl)-1,4,8,11-tetraazacyclotetradecane N,N',N''',N''''-tetraacetic acid (p-nitrobenzyl-TETA), Moi, et al., Anal Biochem., 148, 249-253 (1985); a sexadentate ligand N,N'-dipyridoxyl-ethylenediamine-N,N'-diacetic acid (PLED), Green, et al., Int. J. Nucl. Med. Biol., 12, 381-86 (1985) and N,N'-ethylene-bis[2-(o-hydroxy phenyl)glycine] (EHPG) and N,N'-bis(2-hydroxybenzyl)ethylenediamine-N,N'-diacetic acid (HBED). Taliaferro, et al., Inorg. Chem., 23, 1188-92 (1984).

Preferred chelating agents for use with the present invention include the multidentate chelators based on the 8-hydroxyquinoline chelating unit as well as multidentate chelators with backbone structures based upon tris(2-aminoethyl)amine (TREN) as described in co-owned and copending U.S. Pat. Application Ser. No. 100,390 filed Sep. 24, 1987.

Substrate Reactive Functionalities

Bifunctional chelating agents useful according to the present invention include a substrate reactive moiety capable of participating in a specific binding reaction with at least one functionality present in the antibody molecule to be labelled. The substrate reactive moieties may be reactive with side chain groups of amino acids making up the polypeptide backbone. Such side chain groups include the carboxyl groups of aspartic acid and glutamic acid residues, the amino groups of lysine residues, the aromatic groups of tyrosine and histidine and the sulfhydryl groups of cysteine residues.

Carboxyl side groups presented by the antibody may be reacted with amine substrate reactive moieties of bifunctional chelating agents by means of a soluble carbodiimide reaction. Amino side groups presented by an antibody may be reacted with the isothiocyanate, isocyanate or halotriazine substrate reactive moieties to effect linkage of the chelator to the polypeptide. Alternatively, amino side groups on the antibody may be linked to bifunctional chelating agents bearing amine substrate reactive moieties by means of bifunctional agents such as dialdehydes and imidoesters. Aromatic groups presented by an antibody may be coupled to the chelating agents via a diazonium derivative. Sulfhydryl groups on the antibody molecules may be reacted with maleimides or with haloalkyl substrate reactive groups such as iodoacetamide. Free sulfhydryl groups suitable for such reactions may be generated from the disulfide bonds of the immunoglobulin proteins or may be introduced by chemical derivatization. Linkage to free sulfhydryl groups generated in the intra-heavy chain region of immunoglobulins does not interfere with the antigen binding site of the immunoglobulin but may render the antibody incapable of activating complement.

An alternative method to forming an antibody/chelator linkage via the polypeptide backbone is to form a covalent linkage with the carbohydrate side chains of the glycoprotein according to the methods such as those of Rodwell, et al., U.S. Pat. No. 4,671,958. Thus, the carbohydrate side chains of antibodies may be selectively oxidized to generate aldehydes which may then be reacted either with amine substrate reactive groups to form a Schiff base or with hydrazine, semicarbazide or thiosemicarbazide substrate reactive groups, to give the corresponding hydrazone, semicarbazone or thiosemicarbazone linkages.

An alternative substrate reactive moiety useful for linkage to carbohydrates and polysaccharides without the necessity for prior oxidation is the dihydroxyboryl moiety. This moiety is reactive with substrates containing a 1,2-cis-diol, forming a 5-membered cyclic borate ester, and thus is of use with those carbohydrates, polysaccharides and glycoproteins which contain this group.

Substrate reactive moieties which are useful with chelating agents according to the methods of the present invention include amino (—NH$_2$), diazonium (—NN$^+$), isothiocyanate (—NCS), isocyanate (—NCO), hydrazine (—NHNH$_2$), semicarbazide (—NHCONHNH$_2$), thiosemicarbazide (—NHCSNHNH$_2$), haloacetamide (—NHCOCH$_2$X) including chloro-, bromo- and iodoacetamide, azide (—N$_3$), carboxylate (—CO$_2$H), aminoalkylurea (—NHCONH(CH$_2$)$_n$NH$_2$), aminoalkylthiourea (—NHCSNH(CH$_2$)$_n$NH$_2$), carboxyalkylurea (—NHCONH(CH$_2$)$_n$CO$_2$H) and carboxyalkylthiourea (—NHCSNH(CH$_2$)$_n$CO$_2$H), maleimide, halotriazine including chloro-, bromo- and iodotriazine and meta-(dihydroxyboryl)phenylthiourea (—NHCSNHC$_6$H$_4$-B(OH)$_2$). Other reactive moieties which may be suitable for linking the chelating agents to antibodies include disulfides, nitrenes, sulfonamides, carbodiimides, sulfonyl chlorides, benzimidates, —COCH$_3$ and —SO$_3$H. The preferred substrate reactive moiety for any particular application of this invention will be dictated by the nature of the antibody and by its susceptibility to loss of biological activity as a consequence of forming a given type of linkage.

The substrate reactive moieties useful with the invention may be presented according to a variety of means but have been found to be particularly effective when oriented at the meta or preferably para position on a phenyl group which is attached by means of an aliphatic spacer group to the chelating framework of the invention. The spacer group may consist of from one to about ten carbon atoms, and may be linear or branched alkyl or substituted alkyl provided such branching or substituents do not interfere with the metal binding sites or substrate reactive groups. Linear alkyl linkers are nevertheless preferred with C$_1$ alkyl linkers particularly preferred.

Antibodies are reacted with the substrate reactive moieties of the chelating agents according to the methods disclosed above. Each antibody is preferably bound by more than one chelating agent with chelator to antibody ratios between 2:1 and 5:1 being preferred and chelator to antibody ratios between 3:1 and 5:1 being particularly preferred. The maximum extent of substitution on an antibody, however, is limited by the nature of glycosylation, or the number and location of reactive amino acid side chains on the molecule. Because it is desired that the conjugated protein retain its biological activity, the extent of substitution will be limited according to the nature and position of target glycosylation or amino acid residues both in the primary as well as in the tertiary sequence of the antibody and their degree of involvement in the antigen binding site.

Metal Scavenging Procedure

According to one aspect of the invention, methods are provided for the removal of free, adventitiously bound and chelated metal ions from solutions of antibody/chelator conjugates prior to radiolabelling of the conjugate solution. These methods include the step of exposing the antibody-chelator conjugate solution to high concentrations of an unconjugated chelating agent in a weakly chelating buffer system in order to remove contaminating metal ions and render the chelating moieties available for binding with the metals of the metal labelling solution. After exposure to the unconjugated chelating agent the chelator/antibody conjugate is separated from the solution of unconjugated chelating agent.

Conditions are chosen during the step of exposing the solution of chelator/antibody conjugate to the unconjugated chelating agent such that metal ions present in the conjugate solution or which have become adventitiously bound to the antibody, whether at the specific chelating sites which have been introduced intentionally or at sites within the immunoglobulin molecule which possess intrinsic metal binding properties, are scavenged by the chelating agent to form low molecular weight chelates. These may then be separated from the antibody-chelator conjugate by suitable procedures such as those based on differences in molecular size.

A preferred embodiment employs a dialysis against a buffered solution of free chelating agent as a convenient means of effecting both scavenging and separation, but other methods such as diafiltration or size exclusion chromatography may be employed for those purposes.

The chelating agent used as a scavenger must form metal complexes of sufficient thermodynamic and kinetic stability that it can compete effectively with the antibody-bound chelating groups. Since the nature of the contaminating metals is generally not known, a preferred procedure is to use as a scavenger the same chelating agent that is attached to the antibody. Thus, in the case of an EDTA-antibody conjugate, free EDTA is used as the scavenger whereas for a DTPA-antibody conjugate free DTPA is used, and so forth.

In order to maximize the translocation of contaminating metals from antibody-bound chelating sites to the unconjugated chelating agent, the latter is preferably used in large excess. Useful concentrations of scavenging chelators range from about 0.01 M to about 5 M or higher. The solution of unconjugated chelating agent preferably has a concentration at least an order of magnitude higher and preferably at least two orders of magnitude higher than the chelator concentration of the conjugate in order to provide a sufficient thermodynamic potential for removal of the metal ions. The higher the concentration of the unconjugated chelating agent, the more rapid the removal of free and adventitiously bound metal from the conjugate solution. The maximum concentration of unconjugated chelating agent is limited only by the solubility of the chelating agent. At the same time, however, the greater the concentration of unconjugated chelating agent, the more extensive and time consuming is the step of separating the conjugate solution from that of the unconjugated chelating agent. Practical considerations therefore limit the maximum concentration of unconjugated chelating agent. Preferred concentrations for the unconjugated chelating agent solutions range from about 0.05 M to about 1 M with concentrations of about 0.1 M being most preferred.

The duration of the extraction step during which the chelator/antibody conjugate is exposed to the unconjugated chelating agent is dependent upon the concentration of the solution of unconjugated chelating agent. Solutions having lower concentrations of unconjugated chelating agent require longer periods of exposure to the chelator/antibody conjugate solutions but require less time to extract. Solutions having higher concentrations of unconjugated chelating agent require less time to purge the chelator/antibody conjugate solution of free and adventitiously bound metal ions but require the use of a longer extraction step. Where the solution of unconjugated chelating agent has concentrations of 1 M or greater, the purge step wherein the solution of the chelator/antibody solution is exposed to the solution of unconjugated chelating agent may be carried out in as little as about 12 hours. Where the solution of unconjugated chelating agent has a concentration in the lower end of the range, the purge step may require 72 hours or more. Where a preferred method according to the invention utilizes a solution of unconjugated chelating agent with a concentration of 0.1 M, this solution is preferably exposed to the chelator/antibody conjugate for a period of about 48 hours.

The metal scavenging procedure is carried out in a weakly chelating buffer system. Such a buffer system should have sufficient chelating strength to maintain metal ions in solution and prevent them from precipitating but should not be so strong as to compete for metal ions with the unconjugated chelating agents. Preferred buffers for use with EDTA and DTPA chelating systems typically are characterized by metal binding formation constants of from about $10^6$ to about $10^{12}$ with formation constants from about $10^9$ to about $10^{12}$ being particularly preferred. Where the chelating agent utilized in making up the chelator/antibody conjugate or the unconjugated chelating agent purge solution is a chelator with an extremely high formation constant such as those disclosed in co-owned and copending U.S. Application Ser. No. 100,390 filed Sep. 24, 1987 the weakly chelating solution may have a higher formation constant. Weakly chelating buffers particularly preferred for use with EDTA and DTPA chelating materials include citrate, acetate, nitrilotriacetate and glycine. Suitable concentrations of such buffers range from about 0.01 M to about 0.5 M with concentrations of about 0.01 to about 0.1 M being particularly preferred. The pH of the solutions may range from about 4 to about 10 with particularly preferred pHs being dependent upon the identity of the components present during the reaction procedure as would be determinable by one of skill in the art.

The metal scavenging procedure may be carried out at temperatures ranging from about 2° C. to as high as about 45° C. but is preferably conducted at reduced temperatures in order to prevent denaturation and loss of biological activity of the antibody. Treatment at temperatures ranging from about 2° to about 8° C. is particularly preferred.

After purging the solution of chelator/antibody conjugate by exposure to the solution of unconjugated chelating agent it is necessary to separate the chelator/antibody conjugate from the solution of unconjugated chelating agent. The separation procedure may be carried out by a variety of means as would be obvious to one of skill in the art but is preferably carried out by dialysis. Alternative means could include chromatographic techniques or other methods making use of the difference in size to effect a separation. The degree of separation required will depend in part upon the concentration of unconjugated chelating agent to which the chelator/antibody conjugate was exposed. Where dialysis is used to effect the separation a minimum of 24 hours is generally necessary to remove the unconjugated chelating agent to a sufficient degree. Where the chelator/antibody conjugate solution is purged by exposure to a 0.1 M solution of unconjugated chelating agent a period ranging from about 24 to about 144 hours may be required to separate the conjugate solution from the unconjugated chelating agent.

According to one embodiment of the invention, wherein a solution of chelator/antibody conjugate characterized by having a chelator concentration of greater than about $10^{-4}$ M is produced according to the process of (a) exposing a solution of chelator/antibody conjugate to a solution of unconjugated chelating agent with a concentration greater than about 0.01 M in a weakly chelating buffer for a period greater than about 12 hours, (b) separating the chelator/antibody conjugate from the solution of unconjugated chelating agent, and (c) adjusting the concentration of the antibody bound chelating agent group to greater than about $10^{-4}$ M; the scavenging step is preferably carried out by dialysis. Where this is the case, the solution of chelator/antibody conjugate treated in step (a) is preferably characterized by having a chelator concentration of greater than about $10^{-4}$ M. In such a case it is generally not necessary to adjust the concentration of the antibody chelating group to greater than about $10^{-4}$ M. Where other methods are used in the exposure and separation steps, however, it may be desirable to carry out the exposure or separation steps at dilutions such that the concentration of the antibody bound chelating group is less than about $10^{-4}$ M. In such cases it will then be necessary to adjust the concentration of the conjugate solution such that the the chelator concentration is greater than about $10^{-4}$ M in order that the solution exhibit the unexpected improved properties according to the invention.

Metal Ions

Chelator/antibody conjugate solutions with high metal binding capacity prepared according to the methods and teachings of the present invention may be used to bind a wide variety of metal ions for various diagnostic, therapeutic and other applications. While the metal binding activities and specificities of the conjugate solutions of the invention are dependent upon the particular identities of the conjugated chelating agent it is generally the case that metal ions susceptible to binding by the conjugates of the invention have a valence of three or higher. This is the case because mono- and divalent metals do not generally form sufficiently stable chelates for purposes of the invention.

While contemplated applications of the present invention generally relate to the chelation of radiometal ions, it is of course the case that the materials of the invention may be utilized to bind a variety of non-radioactive metal. Radiometal ions which may be chelated according to the invention include gamma emitter isotopes which are useful for diagnostic scintigraphy. $^{111}$Indium with a half-life of 2.8 days is particularly useful while other suitable gamma emitters include $^{67}$gallium, $^{68}$gallium and $^{99m}$technetium. Beta radiation emitters which are useful as cytotoxic agents for radiotherapy are also useful according to the invention. Such emitters include isotopes such as $^{46}$scandium, $^{47}$scandium, $^{48}$scandium, $^{67}$copper, $^{72}$gallium, $^{73}$gallium, $^{90}$yttrium, $^{97}$ruthenium, $^{100}$palladium, $^{101m}$rhodium, $^{109}$palladium, $^{153}$samarium, $^{186}$rhenium, $^{188}$rhenium, $^{189}$rhenium, $^{198}$gold, $^{212}$radium and $^{212}$lead. Other metal ions useful with the invention include alpha radiation emitting materials such as $^{212}$bismuth, positron emitters such as $^{68}$gallium and $^{89}$zirconium, fluorescent members of the lanthanide series of elements such as terbium and europium and of the transition series such as ruthenium and paramagnetic materials such as gadolinium and iron.

A particular advantage of the high free chelator concentration conjugate solutions of the present invention is their ability to rapidly complex metal solutions with a high binding yield such that low levels of free metal are left in solution. The conjugate solutions are such that they are capable of routinely achieving radiobinding yields in excess of 95% when incubated for thirty minutes or less with the relatively impure radiochemical solutions of $^{111}$indium which are available commercially. The specific binding characteristics of metals other than indium will of course differ from those of that metal. In addition, and perhaps more significantly, solutions of other such metals will contain metal contaminants of differing identities and in differing degrees than those of commercially available $^{111}$indium. As a consequence, conjugate solutions with greater concentrations of free chelator groups may be required to practice the method of producing radiolabelled chelator/antibody conjugates with greater than 95% radiochemical yield where the solution of radiometal contains high levels of metal contaminants.

Complexing of Metal Ions

Methods for forming chelating agent/metal ion conjugates are well known to those of skill in the art. Complexes of the chelating agent and metal ions may generally be formed by incubation of the chelating agent/substrate conjugate with the metal ion in a buffered solution in which the conjugate is physiologically stable. Suitable buffers include those with weak metal-binding properties, such as citrate, acetate or glycine. Appropriate concentrations, temperatures and pH may be selected by one of skill in the art to ensure metal ions bind to the chelating functionality rather than weak binding sites on the substrates. It is particularly desired that all solutions be maintained free of metal impurities.

In one aspect of the present invention, a kit for the preparation of an injectable solution of metal labelled antibody or antibody fragment is provided. Said kit comprises a sterile, apyrogenic solution of an antibody-chelator conjugate containing a maximum number of chelating groups per antibody consistent with retaining immunoreactivity and specificity of the antibody and free from contaminating metals, the conjugate being dissolved at high concentration in a weakly chelating, slightly acidic buffer and said solution being provided in a sterile, apyrogenic container suitable for the aseptic introduction of indium-111 chloride and subsequent aseptic removal of the indium-111 labelled antibody or antibody fragment.

The present invention may be practiced in conjunction with any antibody, polyclonal or monoclonal, and with antibody-chelator conjugates prepared by any of the methods known to the art provided that the method used does not compromise the immunoreactivity of the antibody. Thus, compositions in which the chelating group is an amide derivative of DTPA coupled to an antibody by means of either a mixed anhydride reaction, an active ester reaction or a cyclic anhydride procedure are of utility, as are conjugates in which the chelating group is a benzylthiourea derivative of EDTA or DTPA prepared by reaction of the antibody with the corresponding isothiocyanate derivative. It will be evident to one of skill in the art that the concepts, methods and procedures described herein are also applicable to the labelling of a wide range of other proteins and biologically active substrates with indium-111 and other metals and radiometals in high radiochemical yield. The following examples are therefore intended to be only illustrative of the practice of this invention and are not intended to limit its scope.

EXAMPLE 1

In this example, a monoclonal antibody to carcinoembryonic antigen (CEA) was derivatized with a benzylisothiocyanate derivative of the chelator DTPA to a high level of chelator substitution. The resulting antibody-chelator conjugate was purified to remove contaminating metals and formulated into a composition for indium-111 labelling. The radiochemical yield of indium-111 labelled antibody achieved with this composition was then evaluated by repeated labellings using indium-111 chloride from three different commercial sources.

The IgG$_1$ murine monoclonal antibody to CEA was reacted with N-(carboxymethyl)-N-(2-aminoethyl)-N'-(carboxymethyl)-N'-(2'-bis(carboxymethyl)amino)-ethyl)(4-isothiocyanatophenyl)alanine trihydrochloride, a benzylisothiocyanate derivative of DTPA, as described in detail in co-owned and copending U.S. Pat. Application No. 014,517 filed Feb. 13, 1987, the disclosure of which is herein incorporated by reference. The resulting conjugate was dialysed for 24 hours at from about 2° to about 8° C. against a 0.1 M solution of DTPA in 0.05 M citrate buffer, pH 6.0, then for a further 24 hours against 0.05 M citrate, pH 6.0. The concentration of the conjugate solution was then adjusted to 5 mg/ml and it was aliquoted into acid-washed glass vials, each being sealed with a rubber septum. Analysis of one aliquot of the conjugate by the methods described in the aforementioned copending application revealed that it contained an average of 13 DTPA groups per antibody molecule and retained all of the immunoreactivity of the underivatized antibody.

The vials containing the antibody/chelator conjugate were stored at 2°-8° C. and over the subsequent 146 days a vial was periodically removed from storage and labelled by introducing via syringe 5 mCi of indium-111 chloride (with a concentration ranging between about 30 to 100 mCi/ml as was the case with all the examples presented herein) from one of three sources: New England Nuclear, Billerica, Massachusetts (abbreviated NEN); Medi+ Physics, Richmond, California (abbreviated MP); and Atomic Energy of Canada, Ltd., Kanata, Ontario (abbreviated AEC). After 30 minutes incubation in the vial at room temperature, the yield of indium-111 labelled antibody was determined by thin layer chromatography (TLC) after a DTPA chase, as described by Meares, et al., Anal. Biochem., 142, 68 (1984). A total of 14 such labellings were performed and the results are shown in Table 1.

TABLE 1

| Days post conjugate preparation | Source of indium-111 chloride | % Indium incorporation into antibody |
|---|---|---|
| 0 | MP | 99 |
| 1 | MP | 99 |
| 2 | MP | 98 |
| 3 | AEC | 99 |
| 3 | NEN | 98 |
| 7 | MP | 98 |
| 7 | NEN | 99 |
| 14 | MP | 99 |
| 21 | AEC | 97 |
| 28 | MP | 96 |
| 56 | AEC | 95 |
| 86 | AEC | 95 |
| 116 | AEC | 95 |
| 146 | AEC | 96 |

The mean radiochemical yield of indium-111 labelled antibody over 14 labellings was 97.3% (SE = 1.6%) and the ELISA test described in Example 10 of co-owned and copending application U.S. Ser. No. 014,517 filed Feb. 13, 1987 showed no loss of immunoreactivity in any of the labelled preparations.

EXAMPLE 2

In this example, monoclonal antibody B72.3, the specificity and properties of which have been described in detail by Schlom, et al., Int. J. Cancer, 29, 539 (1982), was derivatized with a benzylisothiocyanate derivative of DTPA, purified to remove contaminating metals and formulated into a composition suitable for indium-111 labelling. As in Example 1, repeated indium-111 labellings were then performed to determine the average radiochemical yield of labelled antibody.

The IgG$_1$ murine monoclonal antibody B72.3 was reacted with the benzylisothiocyanate derivative of DTPA of Example 1, according to the methods described in detail in Example 13 of co-owned and copending U.S. Application Ser. No. 014,517 filed Feb. 13, 1987. The mole ratio of chelating agent to antibody used in the coupling reaction was 7.5:1. The resulting conjugate was dialysed for 24 hours at 2°-8° C. against a 0.1 M solution of DTPA in 0.05 M citrate buffer, pH 6.0, then for a further 24 hours against 0.05 M citrate, pH 6.0. The concentration of the conjugate solution was then adjusted to 5 mg/ml and it was aliquoted into acid-washed glass vials at a volume of 1.0 ml per vial. The vials were then sealed with a rubber septum and stored at 2°-8° C. Analysis of one vial of the resulting B72.3 composition showed that it contained an average of 5 DTPA groups per antibody molecule and retained approximately 60% of the immunoreactivity of underivatized B72.3 as measured by the ELISA method described in the aforementioned copending application.

Over a 58 day period following the preparation, the composition was tested by periodically removing a vial from storage and introducing by syringe 5 mCi of indium-111 chloride (AEC). After a 30 minute incubation at room temperature, the extent of indium-111 incorporation into the antibody was determined according to the method of Meares, et al. A total of nine such labellings were performed and the results appear in Table 2.

TABLE 2

| Days post conjugate preparation | % indium incorporation into antibody |
|---|---|
| 0 | 97 |
| 1 | 97 |
| 2 | 96 |
| 3 | 94 |
| 7 | 93 |
| 14 | 97 |
| 21 | 94 |
| 28 | 96 |
| 58 | 96 |

The mean radiochemical yield of indium-111 labelled B72.3 was 95.5% (SD=1.5%) and the ELISA test revealed no loss of antibody immunoreactivity in the labelled preparations relative to the prelabelling value.

EXAMPLE 3

In this example, the composition of Example 2 was further optimized to avoid the slight loss of immunoreactivity evident at a substitution level of 5 chelators per antibody.

A conjugation of the benzylisothiocyanate derivative of DTPA to monoclonal antibody B72.3 was performed exactly as described in Example 2, except that the mole ratio of chelator to antibody used in the reaction was 5:1. The resulting conjugate was purified and aliquoted into vials according to the methods of Example 2. Subsequent analysis revealed that this composition contained an average of 3 DTPA groups per antibody molecule and retained 100% of the immunoreactivity of underivatized B72.3. When labelled with indium-111 chloride as described in Example 2, this composition gave radiochemical yields of 94 to 97% when tested according to the method of Meares, et al.

EXAMPLE 4

In this example, the composition of Example 3 was labelled with indium-111 and, without any further purification, was injected into nude mice bearing a xenograft of the human colorectal carcinoma line LS174T. The biodistribution of indium-111 activity was then determined at 48 hours post-injection and these data compared with literature values obtained using indium-111 labelled B72.3 compositions which had undergone post-labelling purification to remove nonantibody bound indium-111.

The mouse model used in this example had been described in detail by Colcher, et al., Cancer Res., 44, 5744 (1984) and in the aforementioned copending application. An indium-111 labelled aliquot of the B72.3 composition of Example 3 at a specific activity of 1 $\mu$Ci/$\mu$g was injected into the tail vein of nude mice bearing subcutaneous LS174T tumors, at a dosage of 1 $\mu$g of antibody per mouse. After 48 hours, the mice were sacrificed and the radioactivity in various tissues was determined by counting in a gamma counter. These data appear in Table 3.

TABLE 3

| Tissue | $^{111}$In-B72.3$^{(1)}$ present invention | $^{111}$In-B72.3$^{(2)}$ after Sephadex-G-50 & TSK-3000 HPLC | $^{111}$In-B72.3$^{(3)}$ after TSK-250 HPLC |
|---|---|---|---|
| Blood | 15.74 (6.08) | 18.37 (0.28) | 11.23 (5.51) |
| Tumor | 25.69 (17.24) | 25.94 (1.01) | 42.22 (15.14) |
| Liver | 3.82 (1.23) | 9.09 (0.07) | 19.39 (10.97) |
| Spleen | 4.21 (0.90) | 5.03 (0.09) | 12.12 (7.25) |
| Kidney | 3.20 (1.41) | 8.99 (0.08) | 12.64 (1.66) |
| Lung | 7.09 (2.10) | 9.94 (0.12) | 6.15 (2.52) |

$^{(1)}$Values shown are mean ($\pm$SD) for n = 10.
$^{(2)}$Data from Esteban, et al., J. Nucl. Med., 28, 861 (1987). Values shown are mean ($\pm$SEM) for n = 3 or 4. $^{111}$In labelling was accomplished via a benzylisothiocyanate derivative of DTPA.
$^{(3)}$Data from Brown, et al., Cancer Res., 47, 1149 (1987). Values shown are mean ($\pm$SD) for n = 5. $^{111}$In labelling was accomplished via the bicyclic anhydride of DTPA.

It is apparent from the data in Table 3 that the indium-111 labelled B72.3 composition of the present invention provides a biodistribution pattern that is comparable to, and in some cases superior to, those obtained with indium-111 labelled B72.3 compositions known to the art which have undergone extensive post-labelling purification. Blood levels are generally comparable for all three compositions, as are the tumor uptake values given the high degree of variability inherent in such tumors that is reflected in the standard deviations. Significantly, uptake into organs of the reticuloendothelial system (primarily the liver and spleen) is lowest for the compositions of the present invention, which is advantageous since high uptake into these organs causes severe background problems in scintigraphic studies. The origin of the relatively high kidney activity seen with both prior art compositions is unclear, although this may reflect indium activity which has become separated from the antibody and retained in the kidney by the mechanisms normally involved in resorption of endogeneous metal ions.

EXAMPLE 5

In this example, monoclonal antibody A6H which recognizes an antigen present on renal cell carcinoma and has been described in detail by Vessella, et al., Cancer Res., 45, 6131 (1985), was reacted at varying mole ratios with a benzylisothiocyanate derivative of DTPA in order to establish the optimum number of chelating groups that could be incorporated into this particular IgG molecule without loss of immunoreactivity. The resulting conjugates were purged of contaminating metals then formulated into compositions for indium-111 labelling. Test labellings were then performed in order to evaluate which of the conjugates provided acceptable radiochemical yields of indium-111 labelled A6H.

The IgG$_1$ murine monoclonal antibody in 0.1 M KH$_2$PO$_4$/0.1 M NaHCO$_3$ buffer, pH 8.5, was reacted for 3 hours at 37° C. with varying amounts of the benzylisothiocyanate derivative of DTPA. The resulting antibody-DTPA conjugates were then dialysed for 48 hours at 2°–8° C. against a 0.1 M solution of DTPA in 0.05 M citrate buffer, pH 6.0, then for a further 6 days at 2° to 8° C. against 0.05 M citrate, pH 6.0. The concentration of each conjugate was adjusted to 5 mg/ml then each preparation was evaluated by the cobalt-57 binding assay of Meares, et al., Anal. Biochem., 142, 68 (1984), to assess the average number of chelators per IgG molecule, and by ELISA assays on microtiter plates bearing immmobilized renal cell carcinoma cells, to assess immunoreactivity. Finally, test labellings with indium-111 chloride (AEC) were performed according to the method of Example 1. These data appear in Table 4.

TABLE 4

| Mole ratio of DTPA-SCN:IgG Used in the Conjugation | Average Number of DTPA Groups per IgG Molecule in the Conjugate | % Immuno-reactivity | Radio-chemical yield (%) |
|---|---|---|---|
| 5:1 | 0.5 | 100 | 27 |
| 25:1 | 3.0 | 100 | 98 |
| 50:1 | 3.5 | 100 | 98 |

It is apparent that either of the conjugates obtained at 25:1 and 50:1 mole ratios of chelator to antibody provide acceptable compositions for use without further purification.

EXAMPLE 6

In this example, an IgG$_1$ murine monoclonal antibody raised against the human lung adenocarcinoma cell line, CALU-3, was taken through the optimization procedure described in Example 5. The antibody in 0.1 M KH$_2$PO$_4$/0.1 M NaHCO$_3$ buffer, pH 8.5, was reacted for 3 hours at 37° C. with varying amounts of benzylisothiocyanate derivative of DTPA. The resulting antibody-DTPA conjugates were dialyzed for 48 hours at 2°–8° C. against a 0.1 M solution of DTPA in 0.05 M citrate buffer, pH 6.0. The concentration of each conjugate was then adjusted to 5 mg/ml and each was evaluated by the cobalt-57 binding assay, by ELISA assays on plates coated with immobilized CALU-3 cells and by test labellings with indium-111 chloride according to the method of Example 1. The radiochemical yield of the 6.0:1 chelator to antibody conjugate was determined according to the method of Meares, et al. These data appear in Table 5.

TABLE 5

| Mole ratio of DTPA-SCN:IgG Used in the Conjugation | Average Number of DTPA Groups per IgG Molecule in the Conjugate | % Immuno-reactivity | Radio-chemical yield (%) |
|---|---|---|---|
| 25:1 | 0.1 | 70 | ND |
| 50:1 | 2.2 | 60 | ND |
| 75:1 | 6.0 | 50 | 94 |

EXAMPLE 7

In this example, the F(ab')$_2$ fragment of an IgG$_1$ murine monoclonal antibody to CEA was derivatized with the benzylisothiocyanate derivative of DTPA that was employed in labelling the whole antibodies according to Example 1. The resulting fragment conjugate was purified to remove contaminating metals and formulated into a composition suitable for labelling with indium-111 in high radiochemical yield.

The fragment, at a concentration of 5 mg/ml in 0.1 M $KH_2PO_4/NaHCO_3$ buffer, pH 8.5, was reacted with benzylisothiocyanate derivative at a mole ratio of 40:1 for 3 hours at 37° C. The resulting fragment-DTPA conjugate was then dialysed for 48 hours at 2°-8° C. against a 0.1 M solution of DTPA in 0.05 M citrate buffer, pH 6.0. The concentration of the chelator-fragment conjugate was then adjusted to 5 mg/ml. Subsequent analysis showed that the conjugate retained all of the immunoreactivity of the native (i.e, underivatized) fragment and contained an average of 8 chelating groups per F(ab')$_2$ molecule. A test labelling with indium-111 chloride under the conditions described in Example 1 gave a radiochemical yield of indium-111 labelled fragment of 95% when tested according to the TLC method of Meares, et al.

EXAMPLE 8

In this example, a B72.3-DTPA composition prepared as described in Example 3 was formulated into a "cold" kit for the preparation of an injectable solution of indium-111 labelled B72.3. In this context, a cold kit refers to a composition which is not itself radioactive but which is intended to be mixed with an appropriate radioisotope immediately prior to injection into a patient.

A conjugate composition according to Example 3 was prepared under sterile conditions using depyrogenated buffers and glassware. The resulting solution was filled under sterile conditions into 5 ml glass vials which had been acid washed, baked and sterilized in an autoclave. The fill size was 0.6 ml per vial and the conjugate concentration was 10 mg/ml. Each vial was then sealed with a rubber septum which had been depyrogenated by washing with sodium hydroxide solution and sterilized in an autoclave. The rubber closure was then sealed to the vial by a metal ferrule. Each vial so prepared then constituted a cold kit suitable for the preparation of a single dose of indium-111 labelled B72.3 when used in conjunction with indium-111 chloride supplied by a radioisotope vender.

Test labellings were performed with 5 mCi aliquots of an indium-111 solution on eleven such kits over a 3 month period and radiochemical yields were determined according to the method of Meares, et al. These data appear in Table 6, below.

TABLE 6

| Kit No. | Source of In-111 Chloride | Radiochemical Yield (%) |
|---|---|---|
| 1 | AEC | 95 |
| 2 | AEC | 94 |
| 3 | AEC | 98 |
| 4 | AEC | 98 |
| 5 | NEN | 95 |
| 6 | NEN | 98 |
| 7 | NEN | 97 |
| 8 | NEN | 99 |
| 9 | MP | 97 |
| 10 | MP | 98 |
| 11 | MP | 94 |

The radioisotope suppliers are abbreviated as in Example 1. The mean radiochemical yield of indium-111 B72.3 over all eleven labellings was 96.5% (SD=2%). Each indium-111 labelled dose was tested for pyrogenicity by the USP rabbit pyrogen test and for sterility by culturing out an aliquot of the material. All eleven preparations were found to be sterile and apyrogenic.

EXAMPLE 9

In this example, an anti-CEA monoclonal antibody conjugate with the DTPA isothiocyanate derivative prepared as described in Example 1 was formulated into a "hot" kit for providing an injectable solution of indium-111 labelled anti-CEA. In this context, a hot kit denotes a radiopharmaceutical which is provided to the user in a radioactive form. Thus, unlike a cold kit which must be labelled with the radionuclide on-site by the user, a hot kit involves minimal manipulation of the patient dose by the on-site nuclear pharmacy. Hot kits will typically be prepared on a large scale at a central location and distributed to the end users on demand. This in turn requires that the radiolabelled material possess sufficient stability to permit it to be inventoried for a reasonable period of time. For an indium-111 hot kit, a reasonable production schedule would call for the preparation of one lot per week, such that at the end of the 7 day shelf life, the product would have undergone approximately 3 half-lives of radioactive decay. Therefore, the objective was to develop a hot kit formulation for indium-111 labelled anti-CEA that would retain immunoreactivity and stable binding of the indium label over a period of 7 days postlabelling.

The anti-CEA-DTPA conjugate used in this study contained an average of 4 DTPA groups per antibody. The conjugate was dialysed into 0.05 M citric acid/0.1 M sodium bicarbonate buffer, pH 6.0, and the concentration was adjusted to 5 mg/ml. The conjugate was then labelled with indium-111 by addition of indium-111 chloride and incubation for 30 minutes at room temperature. The resulting indium-111 labelled anti-CEA preparation was aliquoted into vials, at a fill size of 1.0 ml/vial. The initial specific activity was 22.32 mCi per 5 mg of antibody. Because the hot kit requires higher initial specific activity and the addition of increased quantities of $^{111}InCl_3$ introduces elevated levels of acidity to the conjugate solution it was necessary to incorporate a sodium bicarbonate buffer into the conjugate solution so as to prevent the loss of immunological activity as a consequence of lowered pH. The percent of indium-111 specifically bound to the antibody and its immunoreactivity were measured, by the chelator challenge/TLC assay of Meares, et al., and the ELISA assay respectively, immediately post-labelling and at 1, 2, 3, 5 and 7 days. These data appear in Table 7.

TABLE 7

| Days Post-Labelling | % Indium-111 Bound to Antibody | Antibody Immunoreactivity (%) |
|---|---|---|
| 0 | 93 | 100 |
| 1 | 92 | 100 |
| 2 | 95 | 100 |
| 3 | 92 | 100 |
| 5 | 95 | 100 |
| 7 | 94 | 100 |

Since the labelling efficiency and immunoreactivity of the preparation remained unaltered over a 7 day period of storage in solution at 2°-8° C., and since the specific activity after 7 days (4.01 mCi/5 mg) remained within acceptable limits, the formulation of this example constitutes a viable hot kit for the provision of an injectable dose of indium-111 anti-CEA antibody.

EXAMPLE 10

In this example, an anti-CEA conjugate with the benzylisothiocyanate derivative of DTP was prepared, purged of contaminating metal ions and formulated into a composition for radiometal labelling. The resulting composition was then labelled with the gamma-emitting radionuclide, gallium-67.

An anti-CEA-DTPA conjugate was prepared and purified as described in Example 1. The resulting material contained an average of 5 DTPA groups per IgG molecule and retained all of the immunoreactivity of the native anti-CEA antibody. This conjugate, at a concentration of 5 mg/ml in 0.05 M citrate buffer, pH 6.0 was labelled with gallium-67 chloride (New England Nuclear) by mixing 0.1 ml of the conjugate solution with 0.5 mCi of gallium-67 and incubating the resulting solution at room temperature. Aliquots of the solution were removed at 1 hour and 24 hours post-labelling and the radiochemical yield of gallium-67 labelled antibody was assessed using the same chelator challenge/TLC procedure employed in testing the indium-111 labelled conjugates. These data appear in Table 8.

TABLE 8

| Hours Post-Labelling | $\%^{67}Ga$ Incorporation into Antibody |
|---|---|
| 1 | 73 |
| 24 | 95 |

The 95% radiochemical yield attained at 24 hours post-labelling was confirmed by HPLC on a Bio-Rad TSK 250 sizing column. It is concluded that an acceptable gallium-67 labelled anti-CEA composition was obtained that would be suitable for use without additional post-labelling purification.

EXAMPLE 11

In this example, the influence of the concentration of antibody-bound chelating groups on the radiochemical yield of indium-111 labelled antibody was determined for conjugates formed by the benzylisothiocyanate derivative of DTPA with an anti-CEA antibody and with B72.3. The anti-CEA and B72.3 conjugates were prepared and purified as described in Examples 1 and 2, respectively. The anti-CEA-DTPA conjugate contained an average of 5 DTPA groups per IgG molecule and was at an initial concentration of 5 mg/ml in 0.05 M citrate buffer, pH 6.0, (molar concentration of DTPA$=1.56\times10^{-4}$ M). The B72.3-DTPA conjugate contained an average of 3 DTPA groups per IgG molecule and was at an initial concentration of 10 mg/ml in 0.05 M citrate buffer, pH 6.0, (molar concentration of DTPA$=1.88\times10^{-4}$ M). Serial 2-fold dilutions of each conjugate were made in 0.05 M citrate, pH 6.0, as diluent. A 0.1 ml aliquot of each of the resulting solutions was labelled with indium-111 by addition of indium-111 chloride (NEN) and incubation at room temperature for 30 minutes. For B72.3 the amount of added indium-111 chloride was 9 μl (1.2 mCi), for the anti-CEA antibody, 4.5 μl (0.6 mCi of indium-111 activity was used. The radiochemical yield obtained at each concentration was then determined by the chelator challenge/TLC procedure. These data appear in Tables 9 and 10.

TABLE 9

| Molar Concentration of Anti-CEA Bound DTPA Groups | Radiochemical Yield of Indium-111 Anti-CEA (%) |
|---|---|
| $1.56 \times 10^{-4}$ | 98 |
| $7.80 \times 10^{-5}$ | 98 |
| $3.90 \times 10^{-5}$ | 97 |
| $1.95 \times 10^{-5}$ | 98 |
| $9.75 \times 10^{-6}$ | 98 |
| $4.87 \times 10^{-6}$ | 93 |
| $2.43 \times 10^{-6}$ | 18 |
| $1.22 \times 10^{-6}$ | 6 |
| $6.10 \times 10^{-7}$ | 10 |
| $3.05 \times 10^{-7}$ | 1.5 |

TABLE 10

| Molar Concentration of B72.3-Bound DTPA Groups | Radiochemical Yield of Indium-111 B72.3 (%) |
|---|---|
| $1.88 \times 10^{-4}$ | 98 |
| $9.40 \times 10^{-5}$ | 98 |
| $4.70 \times 10^{-5}$ | 98 |
| $2.35 \times 10^{-5}$ | 97 |
| $1.17 \times 10^{-5}$ | 25 |
| $5.87 \times 10^{-6}$ | 10 |
| $2.94 \times 10^{-6}$ | 5 |

It is noteworthy that for each conjugate, there was a narrow and critical chelator concentration range wherein the yield of labelled antibody fell dramatically. It is also noteworthy that this critical concentration was significantly different for B72.3 (approximately $2\times10^{-5}$ M) than it was for the anti-CEA antibody (approximately $4\times10^{-6}$ M). It is highly unlikely that this disparity resulted from the slight difference in the quantities of indium-111 added to each conjugate (1.2 mCi vs. 0.6 mCi).

From the foregoing description, one of skill in the art will recognize numerous changes and modifications of the invention to adapt it do particular usages. Consequently, only such limitations should be placed on the invention as appear in the following claims.

What is claimed is:

1. A method for preparing a chelator/antibody conjugate which can be used to prepare a radioactive metal ion labelled chelator/antibody conjugate which is suitable for in vivo administration to humans without post chelation purification, comprising:
    (a) preparing a chelator/antibody conjugate having an average chelator to antibody substitution level of between about 2 and 15,
    (b) exposing a solution of said chelator/antibody conjugate having an antibody bound chelator concentration of between about $10^{-4}$ M to 1 M, to a solution of unconjugated chelating agents with a concentration both greater than about 0.01 M and at least about ten-fold greater than the concentration of the antibody bound chelator, in a buffer having sufficient chelating strength to maintain metal ions in solution and suitable for transfer of metal ions from the chelator/antibody conjugate to the unconjugated chelating agent, for a period sufficient to effect substantial removal of the metal ions from the chelator/antibody conjugate, and
    (c) separating the chelator/antibody conjugate from the solution of unconjugated chelating agent, and said chelator/antibody conjugate being substantially free of the metal ions.

2. The method according to claim 1 wherein said solution of unconjugated chelating agent has a concentration of from about 0.05 M to about 1 M.

3. The method according to claim 2 wherein said solution of unconjugated chelating agent has a concentration of about 0.1 M.

4. The method according to claim 1 wherein said solution of chelator/antibody conjugate is exposed to said solution of unconjugated chelating agent for a period of from about 24 to about 72 hours.

5. The method according to claim 4 wherein said solution of chelator/antibody conjugate is exposed to said solution of unconjugated chelating agent for a period of about 48 hours.

6. The method according to claim 1 wherein said solution of chelator/antibody conjugate is exposed to said solution of unconjugated chelating agent by means of a dialysis procedure.

7. The method according to claim 6 wherein said dialysis procedure is performed for greater than about 24 hours.

8. The method according to claim 1 wherein said buffer is selected from the group consisting of citrate, acetate, nitrilotriacetate and glycine.

9. The method according to claim 1 wherein said unconjugated chelating agent is the same agent as that conjugated to the antibody in the chelator/antibody conjugate.

10. The method according to claim 1 wherein said solution of unconjugated chelating agent has a concentration about two orders of magnitude greater than the concentration of chelator in the chelator/antibody conjugate.

11. A solution of chelator/antibody conjugate characterized by having an average chelator to antibody substitution level of between about 2 and 15 and by having an antibody bound chelator concentration of between about $10^{-4}$ and 1 M, and produced according to the process of:
  (a) exposing a solution of chelator/antibody conjugate having an antibody bound chelator concentration of between about $10^{-4}$ and 1 M to a solution of unconjugated chelating agent with a concentration both greater than about 0.01 M and at least about ten-fold greater than the concentration of the antibody bound chelator in a buffer having sufficient strength to maintain metal ions in solution and suitable for transfer of metal ions from the chelator/antibody conjugate to the unconjugated chelating agent, for a period sufficient to effect substantial removal of the metal ions from the chelator/antibody conjugate,
  (b) separating and collecting the chelator/antibody conjugate from the solution of unconjugated chelating agent, and
  (c) adjusting the concentration of the antibody bound chelator in the collected chelator/antibody conjugate to between about $10^{-4}$ M and 1 M, and said chelator/antibody conjugate being substantially free of the metal ions.

12. The solution according to claim 11 wherein said solution of unconjugated chelating agent has a concentration of from about 0.05 M to about 1 M.

13. The solution according to claim 12 wherein said solution of unconjugated chelating agent has a concentration of about 0.1 M.

14. The solution according to claim 11 wherein said solution of chelator/antibody conjugate is exposed to said solution of unconjugated chelating agent for a period of about 24 to about 72 hours.

15. The solution according to claim 14 wherein said solution of chelator/antibody conjugate is exposed to said solution of unconjugated chelating agent for a period of about 48 hours.

16. The solution according to claim 11 wherein said solution of chelator/antibody conjugate is exposed to said solution of unconjugated chelating agent by means of a dialysis procedure.

17. The solution according to claim 16 wherein said dialysis procedure is performed for greater than about 24 hours.

18. The solution according to claim 11 wherein said buffer is selected from the group consisting of citrate, acetate, nitrilotriacetate and glycine.

19. The solution according to claim 11 wherein said unconjugated chelating agent is the same agent as that conjugated to the antibody in the chelator-antibody conjugate.

20. The solution according to claim 11 wherein said antibodies retain at least about 50% of their immunoactivity.

21. The solution according to claim 11 wherein said chelator/antibody conjugate is characterized by an average chelator/antibody substitution level between about 3:1 and about 5:1.

22. A method of preparing an aqueous solution of Indium-111 chelator/antibody conjugate comprising less than about 5% free or adventitiously bonded Indium-111 ions and suitable for in vivo administration for radioimmunoscintigraphy purposes, said method comprising the step of incubating under conditions selected for the chelation of indium ions:
  (1) a first solution of chelator/antibody conjugate characterized by having a chelator bound antibody concentration of between about $10^{-4}$ M to 1 M, and produced according to the process of
    (a) exposing a solution of chelator/antibody conjugate having an antibody bound chelator concentration of between about $10^{-4}$ M and 1 M to a solution of unconjugated chelating agent with a concentration both greater than about 0.01 M and at least about ten-fold greater than the concentration of the antibody bound chelator in a buffer having sufficient strength to maintain metal ions in solution and suitable for the transfer of the metal ions from the chelator/antibody conjugate to the unconjugated chelating agent, for a period sufficient to effect substantial removal of the metal ions from the chelator/antibody conjugate,
    (b) separating and collecting the chelator/antibody conjugate from the solution comprising unconjugated chelating agent, and
    (c) adjusting the concentration of the antibody bound chelator in the collected chelator/antibody conjugate to between about $10^{-4}$ M and 1 M, and said chelator/antibody conjugate being substantially free of the metal ions; and
  (2) adding the adjusted chelator/antibody conjugate of step (c) to a second solution of radioactive Indium-111 salt characterized by a radioactivity of greater than about 30 mCi/ml;
  wherein the ratio by volume of said first solution to said second solution is greater than about 5 to 1 and wherein said solutions are incubated for a maximum of 30 minutes.

23. The method according to claim 22 wherein said ratio is greater than about 5 to 1 and less than about 20 to 1.

24. The method according to claim 23 wherein said ratio is about 7 to 1 to about 15 to 1.

25. The method according to claim 22 wherein said chelator is selected from the group consisting of derivatives of diethylenetriaminepentaacetic acid and ethylenediaminetetraacetic acid.

26. The method according to claim 22 wherein said antibody is selected from the group consisting of B72.3 and monoclonal antibodies specific for carcinoembryonic antigen.

27. An Indium-111/chelator/antibody conjugate solution produced according to the method of claim 22.

28. The Indium-111/chelator/antibody conjugate solution according to claim 27 wherein said chelator is selected from the group consisting of derivatives of diethylenetriaminepentaacetic acid and ethylenediaminetetraacetic acid.

29. The Indium-111/chelator/antibody conjugate solution according to claim 27 wherein said antibody is selected from the group consisting of B72.3 and monoclonal antibodies specific for carcinoembryonic antigen.

30. A kit for preparation of an injectable solution of an antibody labelled with a desirable metal comprising:
  (1) a sterile apyrogenic solution of a chelator/antibody conjugate characterized by having an antibody bound chelator concentration of between about $10^{-4}$ and 1 M, and produced according to the process of:
    (a) exposing a solution of chelator/antibody conjugate having an antibody bound chelator concentration of between about $10^{-4}$ M and 1 M to a solution of unconjugated chelating agent with a concentration both greater than about 0.01 M and at least about ten-fold greater than the concentration of the antibody bound chelator in a buffer having sufficient strength to maintain metal ions in solution and suitable for transfer of the metal ions from the chelator/antibody conjugate to the unconjugated chelating agent for a period sufficient to effect substantial removal of the metal ions from the chelator/antibody conjugate,
    (b) separating and collecting the chelator/antibody conjugate from the solution of unconjugated chelating agent,
    (c) adjusting the concentration of the antibody bound chelator in the collected chelator/antibody conjugate to between about $10^{-4}$ and 1 M, and said chelator/antibody conjugate being substantially free of the metal ions; and
  (2) a container which preserves the sterility and apyrogenicity of the solution and has provision for the aspectic introduction of said desirable metal and aseptic removal of the chelator/antibody conjugate labelled with the desirable metal.

31. A kit for preparation of an injectable solution of an antibody labelled with a desirable metal ion comprising:
  (1) a sterile apyrogenic aqueous solution of a desirable metal ion/chelator/antibody conjugate produced by chelation of a first solution containing the desirable metal ion with a second solution of a chelator/antibody conjugate characterized by having an antibody bound chelator concentration of between about $10^{-4}$ M and 1 M, produced according to the process of:
    (a) exposing the second solution of chelator/antibody conjugate having an antibody bound chelator concentration of between about $10^{-4}$ and 1 M to a solution of unconjugated chelating agent in a buffer for a period sufficient to effect substantial removal of undesirable metal ions from the chelator/antibody conjugate,
    wherein concentration of said solution of unconjugated chelating agent is a concentration both greater than about 0.01 M and at least about ten-fold greater than the concentration of the antibody bound chelator in a buffer; said buffer having sufficient strength to maintain the undesirable metal ions in solution and being suitable for transfer of the undesirable metal ions from the chelator/antibody conjugate to the unconjugated chelating agent,
    (b) separating and collecting the chelator/antibody conjugate from the solution of unconjugated chelating agent, and
    (c) adjusting the concentration of the antibody bound chelator in the collected chelator/antibody conjugate to between about $10^{-4}$ and 1 M, and said chelator/antibody conjugate being substantially free of the undesirable metal ions; and
  (2) a container which preserves the sterility and apyrogenicity of the injectable solution and has provision for the aspective introduction and removal of the antibody labelled with the desirable metal ion.

32. The kit according to claim 31 wherein said first solution comprises Indium-111 and is characterized by a radioactivity of greater than about 30 mCi/ml and wherein the ratio by volumes of said second solution to said first solution is greater than about 5 to 1.

33. A method for producing a radioactive metal ion/chelator/antibody conjugate, suitable for in vivo administration without further purification, comprising the steps of:
  (a) preparing a chelator/antibody conjugate having an average chelator to antibody substitution level of between about 2 and 15,
  (b) exposing a solution of said chelator/antibody conjugate having a chelator/antibody conjugate concentration of between about $10^{-4}$ M to 1 M, to a solution of unconjugated chelating agents with a concentration both greater than about 0.01 M and at least about ten-fold greater than the concentration of the chelator/antibody conjugate, in a buffer having sufficient chelating strength to maintain metal ions in solution and suitable for transfer of the metal ions from the chelator/antibody conjugate to the unconjugated chelating agent, for a period sufficient to effect substantial removal of the metal ions from the chelator/antibody conjugate,
  (c) separating the chelator/antibody conjugate from the solution of unconjugated chelating agent, and said chelator/antibody conjugate being substantially free of the metal ions, and
  (d) incubating solution containing said chelator/antibody conjugate of step (c) with a second solution of radioactive metal ions for a period of less than about 30 minutes, where the ratio by volume of the solution containing the chelator/antibody conjugate of step (c) to the second solution is greater than about 5 to 1.

34. The method according to claim 33, wherein the concentration of the antibody bound chelating groups in said purified chelator/antibody conjugate is adjusted to greater than about $10^{-4}$ M.

35. The method according to claim 33, wherein said solution of unconjugated chelating agent has a concentration at least one order of magnitude greater than the concentration of chelator in the chelator/antibody conjugate.

36. The method according to claim 33, wherein said solution of unconjugated chelating agent has a concentration about two orders of magnitude greater than the concentration of chelator in the chelator/antibody conjugate.

* * * * *